(12) United States Patent
Salz et al.

(10) Patent No.: US 7,851,515 B2
(45) Date of Patent: Dec. 14, 2010

(54) HYDROLYSIS-STABLE SELF-ETCHING SINGLE-COMPONENT DENTAL ADHESIVE

(75) Inventors: Ulrich Salz, Lindau (DE); Angela Mucke, Schlins (AT); Jorg Zimmermann, Lustenau (AT); Norbert Moszner, Eschen (LI); Frank Zeuner, Vaduz (LI); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 558 days.

(21) Appl. No.: 11/212,065

(22) Filed: Aug. 25, 2005

(65) Prior Publication Data

US 2006/0130701 A1 Jun. 22, 2006

(30) Foreign Application Priority Data

Dec. 22, 2004 (DE) ........................ 10 2004 061 924

(51) Int. Cl.
  *C07F 9/06* (2006.01)
  *C07F 9/113* (2006.01)
  *C07F 9/143* (2006.01)
  *A61K 6/083* (2006.01)
  *A61K 6/08* (2006.01)
  *A61K 6/00* (2006.01)
  *A61C 5/00* (2006.01)
  *C08F 20/58* (2006.01)
  *C08F 220/54* (2006.01)

(52) U.S. Cl. ........................ 523/115; 523/116; 523/118; 433/228.1; 106/35; 526/303.1; 526/306; 568/8; 522/171

(58) Field of Classification Search .................. 523/115, 523/116, 118; 433/228.1; 106/35; 558/207, 558/214; 526/303.1, 306; 568/8; 522/171
See application file for complete search history.

(56) References Cited

U.S. PATENT DOCUMENTS

| | | | | |
|---|---|---|---|---|
| 4,537,940 A | * | 8/1985 | Omura et al. | 526/278 |
| 4,612,384 A | * | 9/1986 | Omura et al. | 558/198 |
| 5,055,497 A | * | 10/1991 | Okada et al. | 523/116 |
| 5,925,690 A | * | 7/1999 | Fuchigami et al. | 523/118 |
| 6,172,131 B1 | * | 1/2001 | Moszner et al. | 523/116 |
| 2002/0016384 A1 | * | 2/2002 | Moszner et al. | 523/115 |
| 2002/0143138 A1 | * | 10/2002 | Moszner et al. | 528/310 |
| 2002/0198284 A1 | * | 12/2002 | Nakatsuka et al. | 523/116 |
| 2003/0050359 A1 | * | 3/2003 | Kimura et al. | 522/182 |
| 2003/0055124 A1 | * | 3/2003 | Klee et al. | 523/120 |
| 2003/0130373 A1 | * | 7/2003 | Walz et al. | 523/115 |
| 2008/0194730 A1 | * | 8/2008 | Klee et al. | 523/118 |

FOREIGN PATENT DOCUMENTS

| | | |
|---|---|---|
| DE | 100 18 869 | 10/2001 |
| EP | 0 333 503 | 9/1989 |
| EP | 0 712 622 | 5/1996 |
| EP | 1 374 829 | 1/2004 |
| EP | 1 548 021 | 6/2005 |
| WO | WO 03/013444 | 2/2003 |
| WO | WO 3027153 A1 * | 4/2003 |
| WO | WO 03/035013 | 5/2003 |
| WO | WO 2004/060327 | 7/2004 |
| WO | WO 2004/078100 | 9/2004 |
| WO | WO 2005/063778 | 7/2005 |

OTHER PUBLICATIONS

Houben-Weyl, "Methoden der Organischen Chemie," Georg Thieme Verlag, New York, vol. E5, pp. 941-966 (1985).
Houben-Weyl, "Methoden der Organischen Chemie," Georg Thieme Verlag, Stuttgart, vol. XII/2, pp. 158-163 (1964).
Touet et al., "Synthesis of New Acrylic Cation Exchangers Bearing Pendent Alkyl Dihydrogen Phosphate Groups," *Makromol. Chem. Rapid. Commun.* 8:377-382 (1987).
Touet et al., "Synthèse et Copolymèrisation D'acrylamides Comportant le Groupement Dihydroxyphosphoryloxyalkyle," *Makromol. Chem.* 190:313-326 (1989).

* cited by examiner

*Primary Examiner*—Harold Y Pyon
*Assistant Examiner*—Michael Pepitone

(57) ABSTRACT

Dental composition containing (i) at least one acid (meth) acrylamide monomer which has two or more polymerizable groups, (ii) at least one acid monomer which has only one polymerizable group and (iii) at least one polymerization initiator.

13 Claims, No Drawings

HYDROLYSIS-STABLE SELF-ETCHING SINGLE-COMPONENT DENTAL ADHESIVE

The invention relates to compositions which contain at least one acid (meth)acrylamide monomer which has two or more polymerizable groups, and at least one acid hydrolysis-stable monomer which has only one polymerizable group. The compositions are particularly suitable as self-etching, self-conditioning adhesives for dental purposes.

Self-etching, self-conditioning dentin/enamel adhesives normally contain a monomer with an acidic group, optionally one or more non-acidic comonomers and solvents. U.S. Pat. No. 6,147,137 describes for example the combination of acid monomers with hydrophilic monomers such as e.g. 2-hydroxyethyl methylacrylate. Polymerizable acrylates or methacrylates with aromatic carboxylic acid groups are used as acid monomers.

Dental primers which contain olefinically unsaturated monomers with terminal sulfonic acid groups are known from U.S. Pat. No. 6,592,372. The primers are said to be suitable for use in combination with conventional adhesives.

EP 0 333 503 A2 discloses curable compositions which contain a filler which has been treated with polymerizable organic phosphoric or phosponic acid compounds. The compositions can also contain acid monomers.

DE 199 18 974 A1 discloses dental materials based on polymerizable, ethylenically unsaturated monomers which have a phosphonic acid group. These are esters of (meth) acrylic acid.

Dental primer compositions are known from EP 0 811 368 A1 which contain as acid monomers compounds with carboxyl groups, phosphoric acid groups, sulfonic acid groups or phosphonic acid groups. By using a combination of arylborate and transition metal compound as initiator, primers are said to be obtainable which result in a high adhesion upon chemical curing.

DE 101 01 523 A1 discloses dental materials which contain multifunctional amides as cross-linkers, in addition to strongly acidic polymerizable monomers such as phosphoric acid ester methacrylates or acrylophosphonic acids, multifunctional amides as cross-linkers.

WO 03/035013 and WO 03/013444 disclose self-etching, self-conditioning dental adhesives based on (meth)acrylamides containing acid groups, monomers containing sulfonic acid and phosphonic acid groups being preferred.

The acid monomers contained in self-etching, self-conditioning dental adhesives display a strongly acid reaction and encourage hydrolysis reactions in particular in the presence of water, which impairs the stability of the compositions. Therefore acid monomers are stored anhydrous and mostly separated from the other adhesive constituents. The acid monomers are either mixed with the other components shortly before use or applied separately to the tooth surface. With both processes, there is the risk that mistakes will be made during use which lead to clinical failure. For this reason single-component materials are preferred. Although self-etching, self-conditioning single-component systems are already described in the state of the art, they are also shown as losing their function through hydrolytic degradation. A particular problem for the user is that he has no control over the progress of the hydrolytic degradation and thus there is always some uncertainty as regards the clinical success when using such adhesives.

The object of the invention is thus to provide a self-etching single-component adhesive for dental use which is hydrolysis-stable and has a high adhesion to tooth enamel and dentin.

This object is achieved according to the invention by dental compositions which contain the following constituents:
(i) at least one acid (meth)acrylamide monomer which has two or more polymerizable groups,
(ii) at least one acid monomer which has only one polymerizable group, and
(iii) at least one polymerization initiator.

According to a preferred embodiment the compositions additionally contain at least one non-acid (meth)acrylamide monomer (iv) and particularly preferably also a solvent (v). Water, organic solvents miscible with water and mixtures thereof are particularly suitable as solvent. Preferred organic solvents miscible with water are acetone, ethanol and isopropanol.

The compositions can advantageously also contain one or more fillers (vi) for adjusting the rheological properties, improving the mechanical properties and also as an contrast medium. To adjust the Theological properties and to improve the mechanical properties, particulate fillers are preferably used, in particular spherical, amorphous $SiO_2$ particles or mixed-oxide particles of $SiO_2$, $ZrO_2$, tantalum oxide and/or $TiO_2$. These particles are preferably surface-modified with a radically polymerizable silane. Ytterbium trifluoride, barium sulfate or tantalum oxide are preferably used as x-ray opaque fillers. The fillers preferably have a particle size in the range 10-500 nm.

Additionally the compositions can contain one or more further additives (vii). Compositions which contain at least an inhibitor and/or stabilizer as additive are particularly preferred. Advantageous inhibitors and stabilizers are 2,6-di-tert-butyl-4-cresole, methyl hydroquinone or phenothiazine.

The compounds used according to the invention as acid (meth)acrylamide monomers (i) are substances with radically polymerizable acrylamide and/or methacrylamide groups. Substances with 2 to 8 polymerizable groups are particularly preferred, those with 2 to 4 polymerizable groups are most preferred. In the (meth)acrylamide monomers according to the invention the polymerizable ethylene- or (α-methyl)ethylene groups are joined to the rest of the molecule via amide bonds. Monomers with two or more polymerizable groups act as cross-linkers during polymerization and are therefore also called cross-linking monomers in the following. Methacrylamide monomers are particularly preferred.

The monomers (i) preferably contain at least one acid group, particularly preferably 1 to 4 acid groups. Preferred acid groups are phosphorus-containing acid groups, in particular monothiophosphoric acid and quite particularly preferably phosphoric acid groups. Compounds with more than one acid group can contain different acid groups or preferably identical acid groups.

Surprisingly, acidic, cross-linking (meth)acrylamides (i) which contain a phosphoric acid or thiophosphoric acid group and have the following chemical structure have shown themselves to be quite particularly preferable:

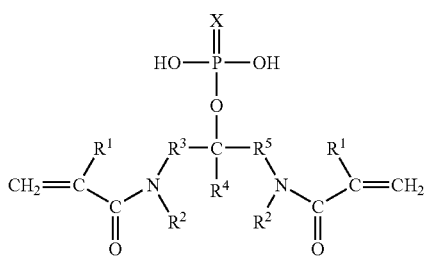

Formula (1)

In Formula 1 the variables have the following meanings:
$R^1$=H, $CH_3$
$R^2$=H, $C_1$-$C_5$ alkyl, $R^3$, $R^5$=independent of each other a $C_1$ to $C_{10}$ alkylene radical, preferably a $C_1$ to $C_5$ alkylene radical and in particular a $C_1$ to $C_3$ alkylene radical, linear radicals being preferred, $R^4$=H or a $C_1$ to $C_{10}$ alkyl radical, preferably a $C_1$ to $C_5$ alkyl radical.

X=O, S.

A particularly preferred example of (meth)acrylamides of formula (1) is 1,3-dimethacrylamido-propane-2-phosphate (DMAPP):

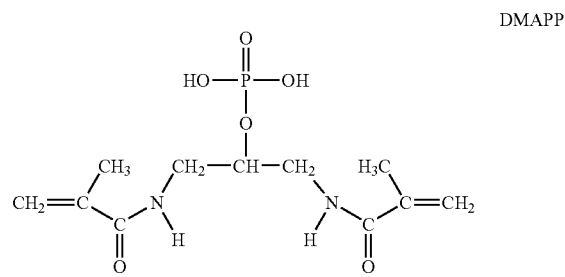

The acid (meth)acrylamide monomers (i) according to the invention of the general formula (1) can be prepared from commercially available diaminoalcohols in a 2-stage reaction. In the first stage the primary ($R^2$=H) or secondary ($R^2$=$C_1$-$C_5$ alkyl) diaminoalcohol reacts with a functional (meth)acrylic acid derivative (chloride, ester, acid or anhydride) using methods known from organic chemistry for linking amide bonds (cf. Methoden der Organischen Chemie [Methods in Organic Chemistry], Houben-Weyl Volume E5 1985, Georg Thieme Verlag pages 941 ff). In the second stage, the bis(meth)acrylamidoalcohol is first reacted with (thio)phosphoryl halide and then in situ with water to give dihydrogen(thio)phosphate (cf. Methoden der Organischen Chemie, HOUBEN-WEYL Volume XII/2 1964, Georg Thieme Verlag Stuttgart, pages 162 ff).

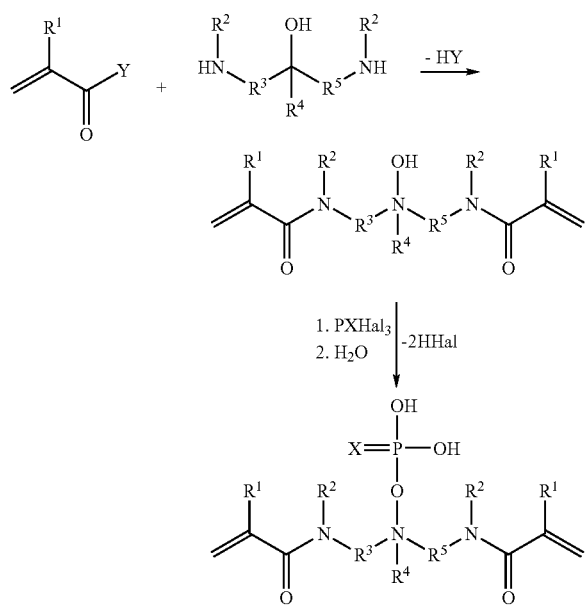

Furthermore it is possible to carry out the phosphorylation at the oxygen starting from a primary ($R^2$=H) or secondary ($R^2$=$C_1$-$C_5$ alkyl) diamino alkanol and then (meth)acrylate the free amino group (J. Touet, C. Pierre, E. Brown, Macromol. Chem., Rapid Comm. 8 (1987) 377 and J. Touet, C. Pierre, E. Brown, Macromol. Chem. 190 (1989) 313).

The monomers (i) are distinguished by high hydrolysis stability. In the context of the present invention compounds described as hydrolysis stable are those stable in water or in mixtures of water and water-miscible solvents at a concentration of approx. 20 wt.-% and a pH value of approx. 2.0 at 37° C. for at least 6 weeks, i.e. hydrolyze less than 5%.

The compounds used according to the invention as acid monomers (ii) are substances with only one radically polymerizable (meth)acrylamide group or α-substituted acryl group. As the monomers (ii) have only one radically polymerizable group they have no cross-linking effect and are therefore also described as non-cross-linking monomers in the following. Hydrolysis-stable compounds are preferred as monomers (ii).

The monomers (ii) preferably contain at least one acid group, particularly preferably 1 to 4 acid groups. Preferred acid groups are carboxylic acid, sulfonic acid, phosphonic acid and/or phosphoric acid groups. Compounds which contain carboxylic acid, phosphonic acid and/or phosphoric acid as acid group are particularly preferred. Compounds with more than one acid group can contain different acid groups or preferably identical acid groups.

Non-cross-linking (meth)acrylamides (ii) which have the following chemical structures have surprisingly proved to be particularly advantageous:

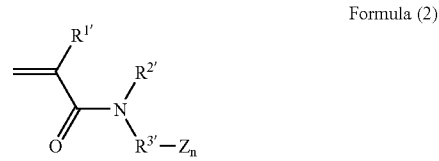

Formula (2)

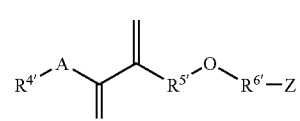

(Formula 3)

In formula (2) the variables have the following meanings:

$R^{1'}$=H, $CH_3$ $R^{2'}$=H, $C_1$-$C_5$ alkyl or $R^{2'}$ forms together with $R^{3'}$ and the nitrogen atom to which it is bonded a heterocycle with 5 to 8, preferably 6 ring atoms, $R^{3'}$=a $C_1$ to $C_{12}$ hydrocarbon radical substituted n fold by Z, preferably $C_2$ to $C_6$ hydrocarbon radical, linear hydrocarbon radicals being particularly preferred, and wherein the hydrocarbon chains of the hydrocarbon radicals can be interrupted by one or more O atoms, or $R^{3'}$ forms together with $R^{2'}$ and the nitrogen atom to which it is bonded a heterocycle with 5 to 8, preferably 6 ring atoms, Z=—P(OH)$_2$(=O), —SO$_3$H, —COOH, —OP(OH)$_2$(=S) or —OP(OH)$_2$(=O), n=1 or 2.

The detail that hydrocarbon, alkyl or alkylene radicals can be interrupted by one or more oxygen atoms is to be understood to mean that one or more oxygen atoms are inserted into the carbon chain of the radicals. The oxygen atoms are each bonded to two neighbouring carbon atoms and thus cannot be terminal. Also, two or more oxygen atoms cannot be bonded to each other.

Preferred compounds of formula (2) are:

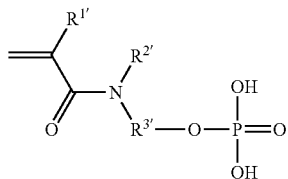

Formula (2a)

the variables being defined as in formula 2. As n has the value 1, $R^{3'}$ is an alkylene radical or forms together with $R^{2'}$ and the nitrogen atom to which it is bonded, a heterocycle, as stated above.

A preferred example of formula (2a) is 1-methacrylamido-hexane-6-dihydrogen phosphate (MHP):

MHP

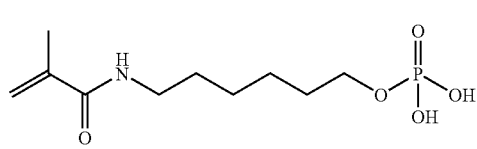

Further preferred compounds of formula (2) are:

Formula (2b)

Formula (2c)

Formula (2d)

the variables R1', R2' and R3' being defined as in formula (2) and formula (2a) and $R^{7'}$=is absent or a $C_1$ to $C_{10}$ alkylene radical, preferably a $C_1$ to $C_6$ alkylene radical, linear alkylene radicals being particularly preferred, $R^{8'}$=a $C_1$ to $C_{10}$ alkyl radical, preferably a $C_1$ to $C_6$ alkyl radical, particularly preferably H, $R^{9'}$=is absent or a $C_1$ to $C_{10}$ alkylene radical, preferably a $C_1$ to $C_6$ alkylene radical, linear alkylene radicals being particularly preferred.

A particularly preferred example of formula (2d) is N-acryloylaspartic acid (AAA):

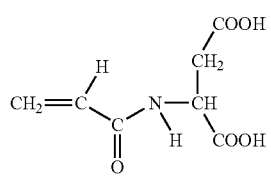

AAA

The acid monomers (ii) of the general formula (2) can be prepared by reaction of primary ($R^{2'}$=H) or secondary ($R^{2'}$=$C_1$-$C_5$ alkyl) amines which contain one or n acid groups Z, with functional (meth)acrylic acid derivatives (chloride, ester, acid or anhydride) using methods known from organic chemistry for linking amide bonds (cf. Methoden der Organischen Chemie, HOUBEN-WEYL Volume E5 1985, Georg Thieme Verlag pages 941 ff and e.g. U.S. Pat. No. 4,157,418).

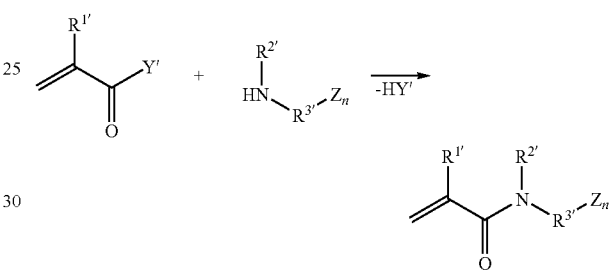

In formula (3) the variables have the following meanings:
A=O, S, NR' with R'=$C_1$ to $C_6$ alkyl,
$R^{4'}$=$C_1$-$C_6$ alkyl, an unsubstituted or substituted phenyl radical,
$R^{5'}$=a $C_1$ to $C_{12}$ alkylene radical, preferably $C_1$ to $C_6$ alkylene radical, linear alkylene radicals being particularly preferred,
$R^{6'}$=a $C_1$ to $C_{12}$ alkylene radical, preferably $C_2$ to $C_6$ alkylene radical, linear alkylene radicals being particularly preferred,
Z=—$SO_3H$, —COOH, —OP(OH)$_2$(=S), —OP(OH)$_2$(=O), preferably —P(OH)$_2$(=O).

The substituents of the phenyl radical are preferably $C_1$ to $C_6$ alkyl groups, particularly preferably $C_1$ to $C_3$ alkyl groups. Substituted phenyl radicals preferably have 1 to 3 substituents.

Quite particularly preferred compounds of formula (3) are:

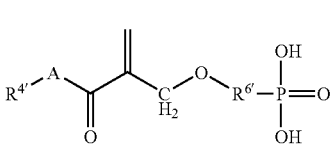

Formula (3a)

the variables having the following meanings:
$R^{4'}$=$C_1$-$C_6$ alkyl, an unsubstituted or substituted phenyl radical,
$R^{6'}$=a $C_1$ to $C_{12}$ alkylene radical, preferably $C_2$ to $C_6$ alkylene radical, linear alkylene radicals being particularly preferred.

Particularly preferred examples of formula (3a) are ethyl 2-[4-(dihydroxyphosphoryl)-2-oxabutyl] acrylate (EAEPA) and 2,4,6 trimethylphenyl 2-[4-(dihydroxyphosphoryl)-2-oxabutyl] acrylate (MAEPA):

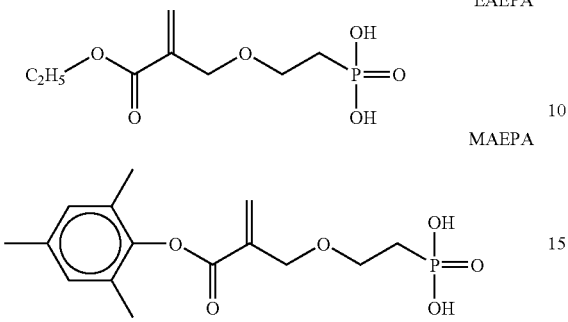

The acid monomers (ii) according to the invention of the general formula (3) can be prepared by reaction of α-halogen methylacrylic acid esters with protected functional phosphonic acid esters followed by regio-selective hydrolysis, as described in DE 197 46 708. The exchange of substituents at the carboxylic acid radical (e.g. for the synthesis of MAEPA) is documented in DE 102 34 326.

Compositions which contain a compound of formula (2) or (3) as acid monomer are preferred according to the invention. Compositions which contain a compound of formula (2) as acid monomer (ii) are particularly preferred, while those which contain a compound of formula (2a) or (2d) are most preferred. Further preferred are compositions which contain a mixture of at least two different compounds according to formulae (2) and/or (3), in particular of formulae (2a), (2b), (2c) and/or (2d), as acid monomer (ii).

The compositions according to the invention preferably contain a monomer with one or more radically polymerizable groups as non-acid (meth)acrylamide monomer (iv).

According to the invention, compositions according to the general formula (4) are particularly preferred as optional, non-acid (meth)acrylamide monomers (iv):

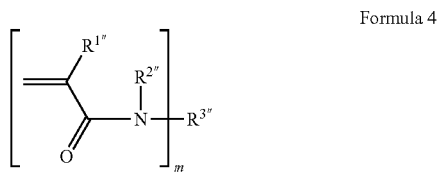

in which
R$^{1''}$=H, CH$_3$,
R$^{2''}$=H, a C$_1$ to C$_{10}$ alkyl radical, preferably a C$_1$ to C$_6$ alkyl radical, or R$^{2''}$ forms together with R$^{3'''}$ and the nitrogen atom to which it is bonded, a heterocycle with 5 to 8, preferably 6 ring atoms,
R$^{3'''}$=a substituted aliphatic C$_1$ to C$_{12}$ hydrocarbon radical, preferably C$_2$ to C$_6$ hydrocarbon radical, linear hydrocarbon radicals being particularly preferred, wherein the carbon chains of the hydrocarbon radicals can be interrupted by one or more O atoms, a C$_6$ to C$_{12}$ arylene or aryl radical or R$^{3'''}$ forms together with R$^{2''}$ and the nitrogen atom to which it is bonded a heterocycle with 5 to 8, preferably 6 ring atoms,
m=1 or 2.

R$^{3'''}$ is substituted m-fold by the radical in brackets. R$^{3'''}$ can be substituted by this radical alone or additionally have further substituents. Hydroxyl groups, in particular 1 to 4 hydroxyl groups, are particularly preferred as further substituents.

If m=1, R$^{3'''}$ is preferably an alkyl radical, particularly preferably a linear alkyl radical, the alkyl radical being able to be substituted by 1 to 4, in particular 1 to 2 hydroxyl groups.

Substances which have the following chemical structure are particularly preferred compounds of type m=1:

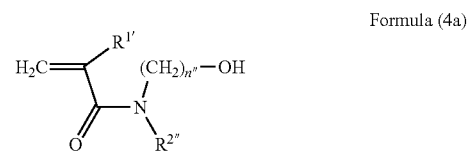

Formula (4a)

wherein
R$^{1'''}$=H, CH$_3$
R$^{2''}$=H, C$_1$-C$_5$ alkyl,
n''=1 to 12, preferably 2 to 10.

Preferred examples of formula (4a) are N-(6-hydroxyhexyl)acrylamide (HHA), N-(5-hydroxypentyl)acrylamide (HPA) and N-(5-hydroxypentyl)methacrylamide (HPMA):

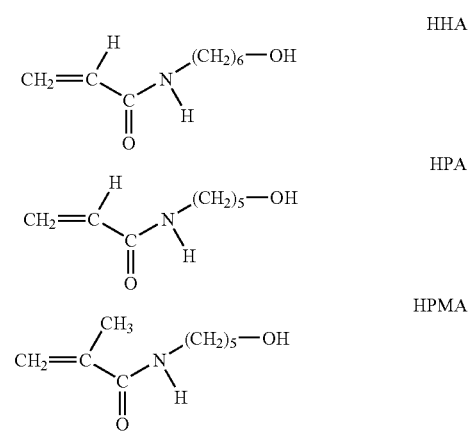

Particularly preferred compounds of the type in which m equals 2 are substances which have the following chemical structure:

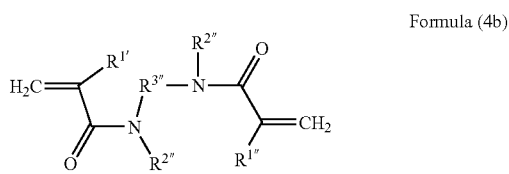

Formula (4b)

wherein
R$^{1'''}$=H, CH$_3$
R$^{2''}$=H, C$_1$ to C$_{10}$ alkyl, preferably C$_1$ to C$_3$ alkyl,
R$^{3'''}$=C$_1$ to C$_{10}$ alkylene, preferably C$_2$ to C$_8$, the alkylene radicals being able to be interrupted by one or more O atoms.

Preferred examples of formula (4b) are N,N'-(diethyl)-1,3-propylene-bis-acrylamide (DEPBA) and N,N'-(dimethyl)-1,6-hexylene-bis-acrylamide (DMHBA):

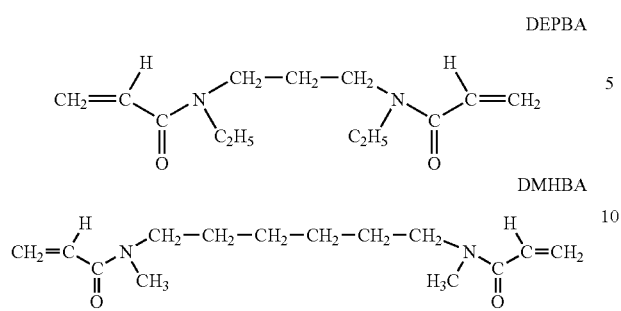

DEPBA

DMHBA

The (meth)acrylamide monomers (iv) according to the invention of the general formula (4) can be prepared by reaction of primary ($R^{2''}$=H) or secondary ($R^{2''}$=$C_1$ to $C_{10}$ alkyl radical) amines with a functional (meth)acrylic acid derivative (chloride, ester, acid or anhydride) using the methods known from organic chemistry for linking amide bonds (cf. Methoden der Organischen Chemie, HOUBEN-WEYL Volume E5 1985, Georg Thieme Verlag, pages 941 ff) and are described i.a. for m=1 in DE 102 28 540 and for m>1 in DE 101 01 523.

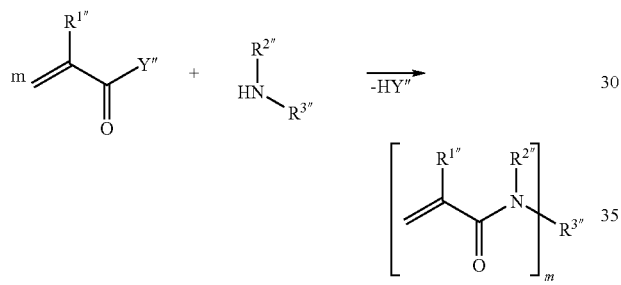

According to the invention compositions are particularly preferred which contain HPA, HPMA and/or DEPBA as (meth)acrylamide, as well as compositions which contain a mixture of monomers with only one polymerizable group and monomers with two and more polymerizable groups. The latter act as additional cross-linkers.

According to the invention, compositions are also particularly preferred which contain, as polymerizable monomers, exclusively (meth)acrylamide derivative and α-substituted acrylates, in particular monomers of the above-mentioned types (i), (ii), (iv). Naturally, compositions which contain the preferred monomers defined above are most preferred.

To initiate the radical polymerization the compositions preferably contain an initiator, particularly preferably a photoinitiator.

Benzophenone, benzoin and derivatives thereof or α-diketones such as 9,10-phenantrenequinone, 1-phenyl-propane-1,2-dione, diacetyl or 4,4-dichlorobenzil are preferably used as photoinitiators. Camphorquinone and 2,2-methoxy-2-phenyl-acetophenone and in particular α-diketones are particularly preferably used in combination with amines as reductants, such as e.g. 4-(dimethylamino)-benzoic acid ester, N,N-dimethylaminoethyl-methacrylate, N,N-dimethyl-sym.-xylidine or triethanolamine.

The compositions according to the invention preferably contain the above-given components in the following quantities, the given quantity ranges can be chosen separately and independently from one another:

1 to 60 wt.-%, preferably 10 to 50 wt.-% (meth)acrylamide (i),
1 to 50 wt.-%, preferably 5 to 40 wt.-% acid monomer (ii),
0.01 to 10 wt.-%, preferably 0.1 to 5 wt.-% polymerization initiator (iii),
1 to 80 wt.-%, preferably 10 to 70 wt.-% (meth)acrylamide (iv),
0 to 80 wt.-%, preferably 10 to 70 wt.-% solvent (v),
0 to 40 wt.-%, preferably 0.5 to 20 wt.-% filler(s) (vi)
0.01 to 10 wt.-%, preferably 0.1 to 5 wt.-% additive(s) (vii).

All values relate, unless otherwise stated, to the total mass of the composition.

The compositions preferably have a pH value in the range of 0.5 to 3.0, particularly preferably 0.5 to 2.0. The self-etching, self-conditioning single-component adhesives according to the invention are distinguished by their high stability to hydrolysis and their good adhesion to tooth enamel and dentin. They are particularly suitable as dental adhesives, in particular for fixing dental materials to dentin and tooth enamel as part of restorative dentistry. They are particularly suitable for use with dental materials which are cured by radical polymerization, in particular composite filling materials, composite fixing materials, fissure sealants, bracket cements, hybrid glass ionomers (methacrylate-reinforced) and radically polymerizing sealing and coating materials.

The invention is further explained in the following with reference to embodiments.

EMBODIMENTS

Examples 1 to 6

Preparation of Dental Adhesives

Adhesives with the compositions given in table 1 were prepared by mixing the starting components. The filler was first dispersed in the solvent. The initiators/stabilizers were dissolved in a mixture of liquid monomer and solvent. A homogeneous adhesive mixture was obtained by mixing all constituents accompanied by stirring, solid monomers dissolving in the mixture.

The adhesion of the adhesive to tooth enamel and dentin was then determined. Bovine teeth were embedded in plastic cylinders in such a way that the dentin or tooth enamel and the embedding plastic were at one level. A microbrush was used to rub the adhesive in question for 30 s into the surface to be treated, this was dried with an air blower and lit for 20 s with a conventional dental polymerization lamp. Using a Delrin Form, a plug comprising 2 layers of a dental composite (Tetric Ceram, Ivoclar Vivadent AG) was applied to the adhesive layer, each composite layer being lit for 40 s each time. The testpieces were then stored in water for 24 h at 37° C. and then the adhesive shear strength measured according to ISO guideline "ISO 1994-ISO TR 11405: Dental Materials Guidance on Testing of Adhesion to Tooth Structure". The found results are also given in table 1.

Examples 7 to 9

Production of Dental Adhesives (Comparison)

Analogously to examples 1 to 6, dental adhesives were prepared which contained either only a (meth)acrylate monomer (i) (example 8) or an acid monomer (ii) (examples 7 and 9). The compositions of the adhesives are given in table 2.

Subsequently, adhesion to tooth enamel and dentin was determined as described in examples 1 to 6. The found results are also shown in table 2.

Table 1 shows that the compositions according to the invention have an advantageous combination of properties. In addition to a good hydrolysis stability they show high adhesive on tooth enamel and dentin. While compositions differing from this (table 2) also show a good hydrolysis stability, they have a clearly lower adhesive action.

TABLE 1

| Constituent | | Ex. 1 [wt.-%] | Ex. 2 [wt.-%] | Ex. 3 [wt.-%] | Ex. 4 [wt.-%] | Ex. 5 [wt.-%] | Ex. 6 [wt.-%] |
|---|---|---|---|---|---|---|---|
| cross-linking acidic monomer (i) | DMAPP | 15.0 | 14.6 | 9.0 | 12.0 | 14.0 | 12.0 |
| non-cross-linking acid monomer (ii) | MHP | 10.0 | — | — | — | — | — |
| | AAA | — | 9.7 | 10.0 | 8.0 | — | 8.0 |
| | MAEPA | — | — | — | — | 9.0 | — |
| cross-linking non-acid monomer (iv) | DEPBA | 49.07 | 47.77 | 36.07 | 39.0 | — | 39.0 |
| | DMHBA | — | — | — | — | 46.0 | — |
| non-cross-linking non-acid monomer (iv) | HHA | — | 2.0 | 15.0 | — | — | — |
| | HPMA | — | — | — | 15.0 | 5.0 | — |
| | HPA | — | — | — | — | — | 15.0 |
| solvent | water | 24.0 | 24.0 | 21.0 | 24.0 | 24.0 | 24.0 |
| | acetone | — | — | 7.0 | — | — | — |
| Filler | A200 | 1.0 | 1.0 | 1.0 | 1.0 | 1.0 | 1.0 |
| initiator/stabilizer | BHT | 0.03 | 0.03 | 0.03 | 0.03 | 0.03 | 0.03 |
| | EMBO | 0.5 | 0.5 | 0.5 | 0.5 | 0.5 | 0.5 |
| | CC | 0.4 | 0.4 | 0.4 | 0.4 | 0.4 | 0.4 |
| coefficient of adhesion | | [MPa] | [MPa] | [MPa] | [MPa] | [MPa] | [MPa] |
| enamel | | 17.4 | 21.7 | 21.0 | 16.9 | 13.8 | 17.9 |
| dentin | | 23.2 | 23.8 | 21.3 | 21.0 | 19.1 | 19.1 |

Abbreviations: A200=Aerosil A200 Degussa; BHT=2,6-di-tert-butyl-4-cresol; CC=camphorquinone; EMBO=ethyl-4-dimethyl-aminobenzoate

TABLE 2

(Comparison examples)

| Constituent | | Ex. 7 [wt.-%] | Ex. 8 [wt.-%] | Ex. 9 [wt.-%] |
|---|---|---|---|---|
| cross-linking acid monomer (i) | DMAPP | — | 37.6 | — |
| non-cross-linking acid monomer (ii) | AHP | 20.9 | — | — |
| | AAA | — | — | 15.07 |
| cross-linking non-acid monomer (iv) | DEPBA | 32.6 | — | 19.0 |
| non-cross-linking non-acid monomer (iv) | HHA | 12.4 | 32.4 | 25.0 |
| solvent | water | 18.2 | 28.07 | 30.0 |
| | acetone | — | — | 9.0 |
| | ethanol | 13.97 | — | — |
| filler | A200 | 1.0 | 1.0 | 1.0 |
| initiator/stabilizer | BHT | 0.03 | 0.03 | 0.03 |
| | EMBO | 0.5 | 0.5 | 0.5 |
| | CC | 0.4 | 0.4 | 0.4 |
| coefficient of adhesion | | [MPa] | [MPa] | [MPa] |
| enamel | | 9.4 | 7.7 | 7.0 |
| dentin | | 12.3 | 13.8 | 11.3 |

Abbreviations: A200=Aerosil A200 Degussa; BHT—2,6-di-tert-butyl-4-cresol; CC=camphorquinone; EMBO=ethyl-4-dimethyl-aminobenzoate

The invention claimed is:

1. Dental composition containing 1 to 60 wt.-% of at least one acid (meth)acrylamide monomer which has two or more polymerizable groups, (ii) 1 to 50 wt.-% of at least one acid monomer which has only one polymerizable group, (iii) 0.01 to 10 wt.-% of at least one polymerization initiator, and (iv) 1 to 80 wt.-% of at least one non-acid (meth)acrylamide monomer, wherein the (meth)acrylamide (i) is 1,3-dimethacrylamido-propane-2-phosphate

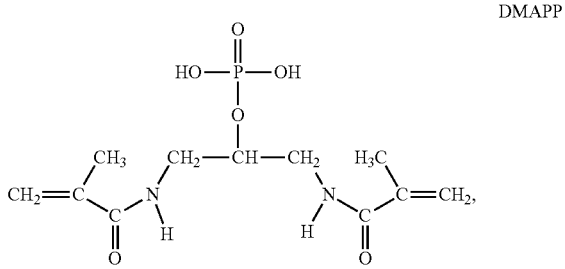

DMAPP wherein the monomer (ii) is a compound according to the following formula (2):

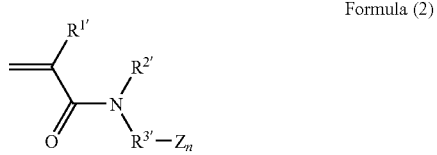

Formula (2)

in which $R^{1'}$=H, $CH_3$, $R^{2'}$=H, $C_1$-$C_5$ alkyl or $R^{2'}$ forms together with $R^{3'}$ and the nitrogen atom to which it is bonded, a heterocycle with 5 to 8 ring atoms, $R^{3'}$=an aliphatic $C_1$ to $C_{12}$ hydrocarbon radical n-fold substituted by Z, wherein the carbon chains of the hydrocarbon radicals can be interrupted by one or more O atoms or $R^{3'}$ forms together with $R^{2'}$ and the nitrogen atom to which it is bonded a heterocycle with 5 to 8 ring atoms, $Z=$ —$P(OH)_2(=O)$, —$SO_3H$, —$COOH$, —$OP(OH)_2(=S)$ or —$OP(OH)_2(=O)$;

$n=1$ or 2; and/or the acid monomer (ii) is a compound according to formula (3):

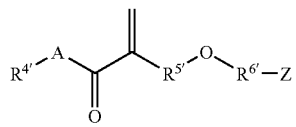

Formula (3)

in which $A=O, S, NR$ with $R=C_1$ to $C_6$ alkyl, $R^{4'}=C_1-C_6$ alkyl, an unsubstituted or substituted phenyl radical, $R^{5'}=$ a $C_1$ to $C_{12}$ alkylene radical, $R^{6'}=$ a $C_1$ to $C_{12}$ alkylene radical, $Z=$ —$SO_3H$, —$COOH$, —$OP(OH)_2(=S)$, —$OP(OH)_2(=O)$ or —$P(OH)_2(=O)$, and wherein the monomer (iv) is N,N'-(diethyl)-1,3-propylene-bis-acrylamide

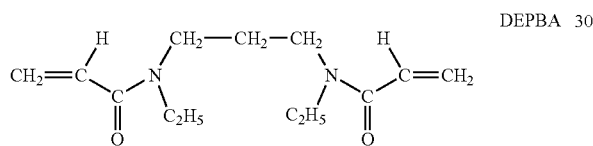

DEPBA or N,N'-(dimethyl)-1,6-hexylene-bis-acrylamide

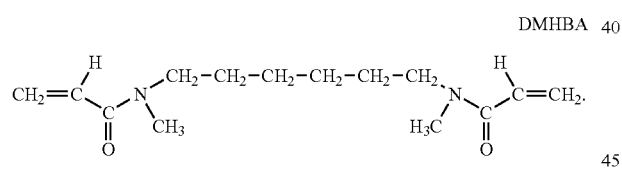

DMHBA

2. Composition according to claim 1, which additionally contains solvent.

3. Composition according to claim 2, which contains as solvent water and/or an organic solvent miscible with water.

4. Composition according to claim 1, which additionally contains up to 40 wt.-% of at least one filler.

5. Composition according to claim 1, which additionally contains as an additive at least one inhibitor and/or stabilizer.

6. Composition according to claim 1, which contains as acid monomer (ii) a mixture of at least two different monomers of formula (2).

7. Composition according to claim 1, further containing
0 to 80 wt.-% solvent (v), and
0 to 40 wt.-% filler(s) (vi).

8. System comprising a composition according to claim 1 and a dental material curable by radical polymerization.

9. System according to claim 8 in which the dental material is a composite filling material, composite fixing material, fissure sealant, bracket cement, methacrylate-reinforced hybrid glass ionomer, a sealing material or coating material.

10. A method for the fixing of a radically polymerizable dental material to tooth enamel and/or dentin comprising applying the composition of claim 1 and a dental material curable by radical polymerization to tooth enamel and/or dentin and polymerizing said dental material.

11. A composition comprising a self-etching, single-component dental adhesive containing:
(i) 1 to 60 wt.-% of at least one acid (meth)acrylamide monomer which has two or more polymerizable groups,
(ii) 1 to 50 wt.-% of at least one acid monomer which has only one polymerizable group,
(iii) 0.01 to 10 wt.-% of at least one polymerization initiator, and
(iv) 1 to 80 wt.-% of at least one non-acid (meth)acrylamide monomer, wherein the (meth)acrylamide (i) is 1,3-dimethacrylamido-propane-2-phosphate

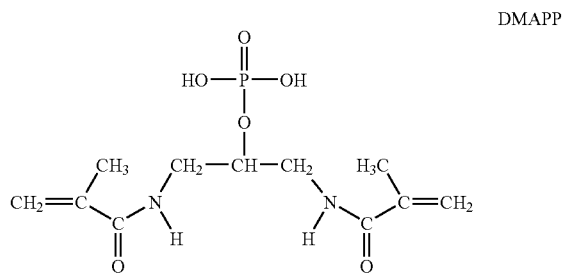

DMAPP the monomer (ii) is a compound according to the following formula (2):

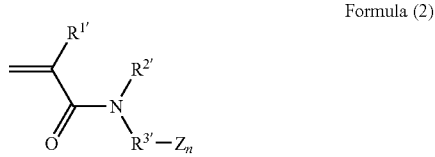

Formula (2)

in which $R^{1'}=H, CH_3$, $R^{2'}=H, C_1-C_5$ alkyl or $R^{2'}$ forms together with $R^{3'}$ and the nitrogen atom to which it is bonded, a heterocycle with 5 to 8 ring atoms, $R^{3'}=$ an aliphatic $C_1$ to $C_{12}$ hydrocarbon radical n-fold substituted by Z, wherein the carbon chains of the hydrocarbon radicals can be interrupted by one or more O atoms or $R^{3'}$ forms together with $R^{2'}$ and the nitrogen atom to which it is bonded a heterocycle with 5 to 8 ring atoms, $Z=$ —$P(OH)_2(=O)$, —$SO_3H$, —$COOH$, —$OP(OH)_2(=S)$ or —$O P(OH)_2(=O)$;

$n=1$ or 2; and/or the acid monomer (ii) is a compound according to formula (3):

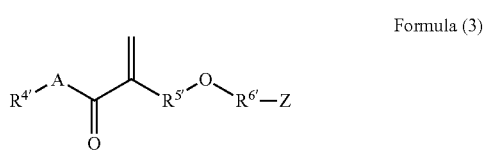

Formula (3)

in which $A=O, S, NR$ with $R=C_1$ to $C_6$ alkyl, $R^{4'}=C_1-C_6$ alkyl, an unsubstituted or substituted phenyl radical, $R^{5'}$ = a $C_1$ to $C_{12}$ alkylene radical,
$R^{6'}$ = a $C_1$ to $C_{12}$ alkylene radical,
$Z$ = —$SO_3H$, —COOH, —$OP(OH)_2$(=S), —$OP(OH)_2$(=O) or —$P(OH)_2$(=O); and
wherein
the non-acid (meth)acrylamide monomer (iv) is N,N'-(diethyl)-1,3-propylene-bis-acrylamide

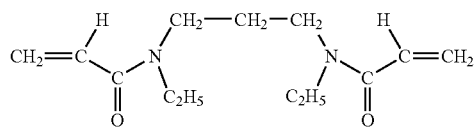

DEPBA or N,N'-(dimethyl)-1,6-hexylene-bis-acrylamide

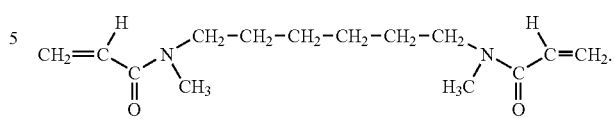

DMHBA

12. Composition according to claim 1, wherein the bond strength of an adhesive prepared from such a composition to enamel and/or dentin is at least 13.8 MPa.

13. Composition according to claim 11, further comprising up to 40 wt.-% of at least one filler.

* * * * *